United States Patent [19]

Urie et al.

[11] Patent Number: 4,722,830

[45] Date of Patent: Feb. 2, 1988

[54] AUTOMATED MULTIPLE STREAM ANALYSIS SYSTEM

[75] Inventors: Michael W. Urie; William A. Young, both of Wilmington, N.C.

[73] Assignee: General Electric Company, San Jose, Calif.

[21] Appl. No.: 859,544

[22] Filed: May 5, 1986

[51] Int. Cl.⁴ ............................................. G01N 35/04
[52] U.S. Cl. .................................. 422/62; 73/863.73; 422/81; 422/103
[58] Field of Search ............... 422/67, 73, 103, 62, 422/81; 73/864.63, 864.64, 864.65, 863.71, 863.72, 863.73

[56] References Cited

U.S. PATENT DOCUMENTS

| | | | |
|---|---|---|---|
| 3,116,642 | 1/1964 | Weir | 73/863.73 |
| 3,943,363 | 3/1976 | Amblard | 250/288 |
| 4,127,111 | 11/1978 | Drolet | 422/81 |
| 4,207,465 | 6/1980 | Favre et al. | 250/288 |
| 4,229,971 | 10/1980 | Ririe, Jr. | 73/61 R |
| 4,361,538 | 11/1982 | Dicoi et al. | 422/62 |
| 4,424,559 | 1/1984 | Lorincz et al. | 422/62 |
| 4,472,354 | 9/1984 | Passell et al. | 422/62 |
| 4,558,946 | 12/1985 | Galle et al. | 422/73 |

*Primary Examiner*—Michael S. Marcus
*Attorney, Agent, or Firm*—Robert R. Schroeder; Raymond G. Simkins

[57] ABSTRACT

An automated analysis system includes a pair of sample selection subsystems whose operations are coordinated by a host computer pursuant to developing analytical data useful to a process computer in controlling an industrial process. Each subsystem includes a sample selection computer operating to control one or more multiport valves in extracting fluid samples on a scheduled or demand basis from sample loops connected with the various process streams involved with the process. The extracted samples are injected into a spectrometer for analysis. An instrument computer converts the spectrometer responses to analytical data indicative of the constituent concentrations found in an analyzed sample.

10 Claims, 4 Drawing Figures

AUTOMATED MULTIPLE STREAM ANALYSIS SYSTEM

The present invention relates to an analytical system for automatically monitoring process and/or waste streams in an industrial process pursuant to controllably optimizing the operations thereof.

Analysis of the constituents in an industrial process stream or streams can provide important analytical information regarding the operating condition of the process. Such information can provide the basis for automatically controlling valves, pumps, reactions, etc., pursuant to optimizing the process. Increased output of a higher quality product can thus be achieved. In addition, such analytical information can indicate the existence of constituent concentrations which exceed or fall below nominal limits and serve to initiate appropriate action which in extreme cases may involve a shutdown of the process. The source of a malfunction may be readily identified such that repair is expedited, and thus downtime is minimized. By comparing the analytical data over a period of time, a degradation trend can be identified such that appropriate maintenance procedures can be conveniently scheduled before the problems become serious.

While it is obviously important to monitor the process streams involving the product being manufactured, it is also equally important to monitor the waste streams given off by the process. Analytical data regarding such waste or effluent streams typically provides an indication of the efficiency of the process. It would also be beneficial to know if and to what extent the product is being lost in the waste streams. If the product is particularly valuable, its recovery from the waste streams is probably a cost-justified measure. Moreover, if the waste streams contain hazardous elements, expensive treatment procedures to render them environmentally safe must be implemented. Otherwise, costly and regulated disposal procedures must be followed. Analytical data regarding the waste stream constituents can advantageously be used to control both the product recovery process and the waste treatment process.

To be of maximum benefit, the analytical data should be as current as possible. Thus, the gathering and evaluation of this data should be performed on a real-time basis for best results. Continuous monitoring of a stream would be ideal; however, typically plural streams or plural points along a single stream need to be monitored. This would indeed be the case if product, waste, recovery and treatment streams are all to be monitored. Continuous monitoring of all of these streams would require an analytical detector devoted to each monitoring point. In many process applications, it is necessary to monitor the various streams for not only the presence of a plurality of elements, but also the concentrations of each. A single analytical device capable of analyzing for all of the elements of interest or a separate device for each element duplicated at each monitoring point makes continuous real-time monitoring a very costly approach. This is particularly so when useful analytical data calls for analyses down to concentrations in parts per million or even per billion, requiring expensive, highly sophisticated analytical instrumentation. Fortunately, the vast majority of process applications do not require continuous monitoring of plural streams, and thus analyses performed serially utilizing a single or at least a minimal number of analytical devices (plural element analysis) on a time-shared basis is an acceptable approach. In this case, it is important that the samplings be taken frequently and the analyses be conducted rapidly such that the analytical data represents a reasonably current or real-time analysis of the stream constituents of interest.

It is accordingly an object of the present invention to an improved automated system for performing chemical analysis on a plurality of process streams.

An additional object is to provide a system of the above-character wherein analytical data pertaining to the concentrations of plural constituents is developed rapidly on a real-time basis.

A further object is to provide a system of the above-character wherein samplings from a plurality of streams are taken for analysis in accordance with a predetermined schedule.

Yet another object of the present invention to provide a system of the above-character wherein a sampling schedule may be interrupted on demand to take a sample from any selected stream for analysis.

An additional object is to provide a system of the above-character wherein cross-contamination between consecutive samples is avoided.

A further object is to provide a system of the above character wherein standardization of the analytical device or devices is performed automatically.

Yet another object is to provide a system of the above character wherein the integrity of each sample is preserved.

Another object is to provide a system of the above-character wherein the analytical data is utilized to control a process or processes involving the various streams.

Other objects of the invention will in part be obvious and in part appear hereinafter.

SUMMARY OF THE INVENTION

In accordance with the present invention, there is provided an automated, on-line system for analyzing the concentrations of plural constituents in a plurality of process streams. The resulting analytical data is processed and utilized for process control, signalling abnormal operating conditions, and reporting results. The various process streams to be monitored are each equipped with a sampling loop through which a shunted portion of the fluid stream continuously flows. These sample loops are piped through different ports of a multiport valve included in a sample selection subsystem whose operation is normally automated by a computer pursuant to a predetermined sample selection schedule. This sample selection computer controllably operates the multiport valve to extract a sample from a selected stream which is routed to an analytical instrument for chemical analysis. Analytical data pertaining to the analysis results is compared with an appropriate analytical control table in the sample selection computer to identify any off-limits constituent concentrations. The multiport valve is also computer controlled to inject rinse solutions for sample cross-contamination prevention and to inject standard solution for analytical instrument calibration. The sample selection computer also accepts requests from an operator and from a process control computer to take a sample from any selected stream. Provision is also made to take a sample from a manually collected specimen for analysis.

To expand capacity and to accommodate more frequent samplings, there is provided a pair of sample selection subsystems whose automated operations are coordinated by a host computer. Each subsystem is assigned primary responsibility for different groups of process streams, however both subsystems have the capability to sample all process streams for complete redundancy. As a consequence, the ability to timely provide analytical data necessary for process control is not jeopardized while one of the subsystems is occupied with running an instrument calibration routine or is down for maintenance and repair. The computer controlling the process responsible for the various process streams communicates with the host computer and directly with the sample selection computers, and thus real-time process control is not jeopardized should the host computer go down.

The invention accordingly comprises the features of construction, combination of elements and arrangement of parts, all of which will be exemplified in the following detailed description, and the scope of the invention will be indicated in the claims.

BRIEF DESCRIPTION OF THE DRAWINGS

For a full understanding of the nature and objects of the present invention, reference may be had to the following detailed description taken in conjunction with the accompanying drawings, in which.

Like reference numerals refer to corresponding parts throughout the several views of the drawings.

DETAILED DESCRIPTION

Figure 1:
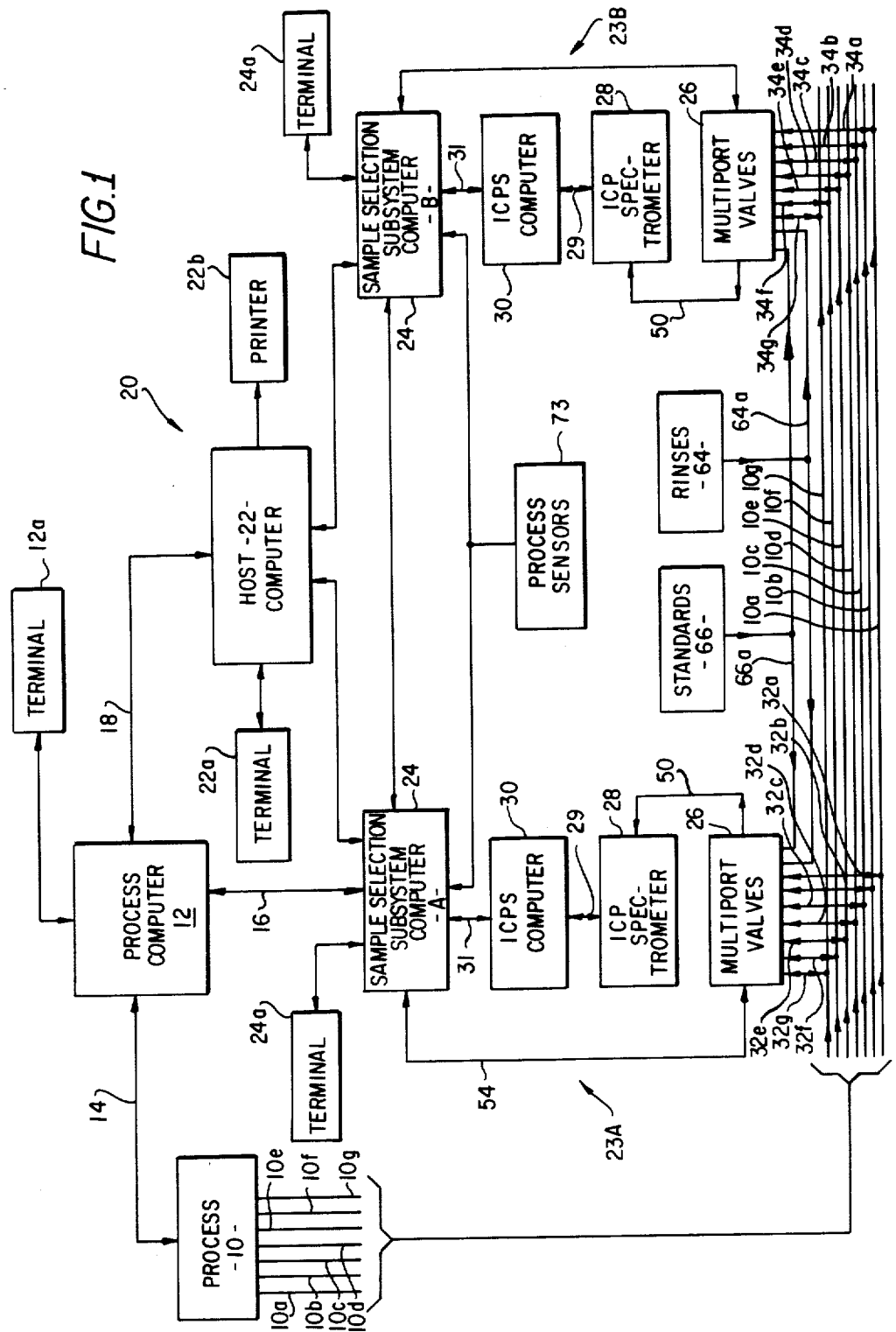
FIG. 1 is a schematic block diagram of an automated multiple stream analysis system constructed in accordance with the present invention.

Referring to FIG. 1, reference numeral 10 generally refers to an industrial process for producing a desired product. In practice, process 10 may represent several related processes such as a product producing process, together with a product recovery process and a waste treatment process concerned with effluents from the product process. Involved with process or processes 10 are a plurality of process streams 10a–10g consisting of fluids flowing in pipes, conduits, reactors, etc. Controlling the multiplicity of valves, pumps, etc. involved in process 10 is a process computer 12 via a multitude of signal paths commonly indicated at 14. Signals are also transmitted back to the process computer to provide information as to a variety of conditions existing in the process, such as temperature, pressure, flow rates, etc., as well as feedback signals indicating that the computer commands are indeed being executed.

Connected in communication with process computer 10 via data links 16 and 18 is an automated multiple stream analysis system, generally indicated at 20. This system is seen to include a host computer 22 and a pair of identically configured sample selection subsystems generally indicated at 23A and 23B. Each of these subsystems includes a computer 24, a plurality of multiport valves commonly indicated at 26, an analytical instrument, such as an inductively coupled plasma spectrometer 28, and its associated computer 30. As seen in FIG. 1, sample loops 32a through 32g are connected to shunt representative portions of the fluids flowing in streams 10a through 10g, respectively, to multiport valves 26 of sample selection subsystem 23A, while sample loops 34a through 34g shunt representative portions of the fluids flowing in streams 10a through 10g, respectively, to multiport valves 26 of subsystem 23B. Thus, the multiport valves of both subsystems 23A and 23B are capable of taking samples from all of the process streams 10a through 10g for full redundancy, however normally the sampling load is shared between the two subsystems under the control of host computer 22. This insures that all process streams can be monitored even though one of the subsystems is down for servicing or occupied in an instrument calibration routine.

Figure 3:
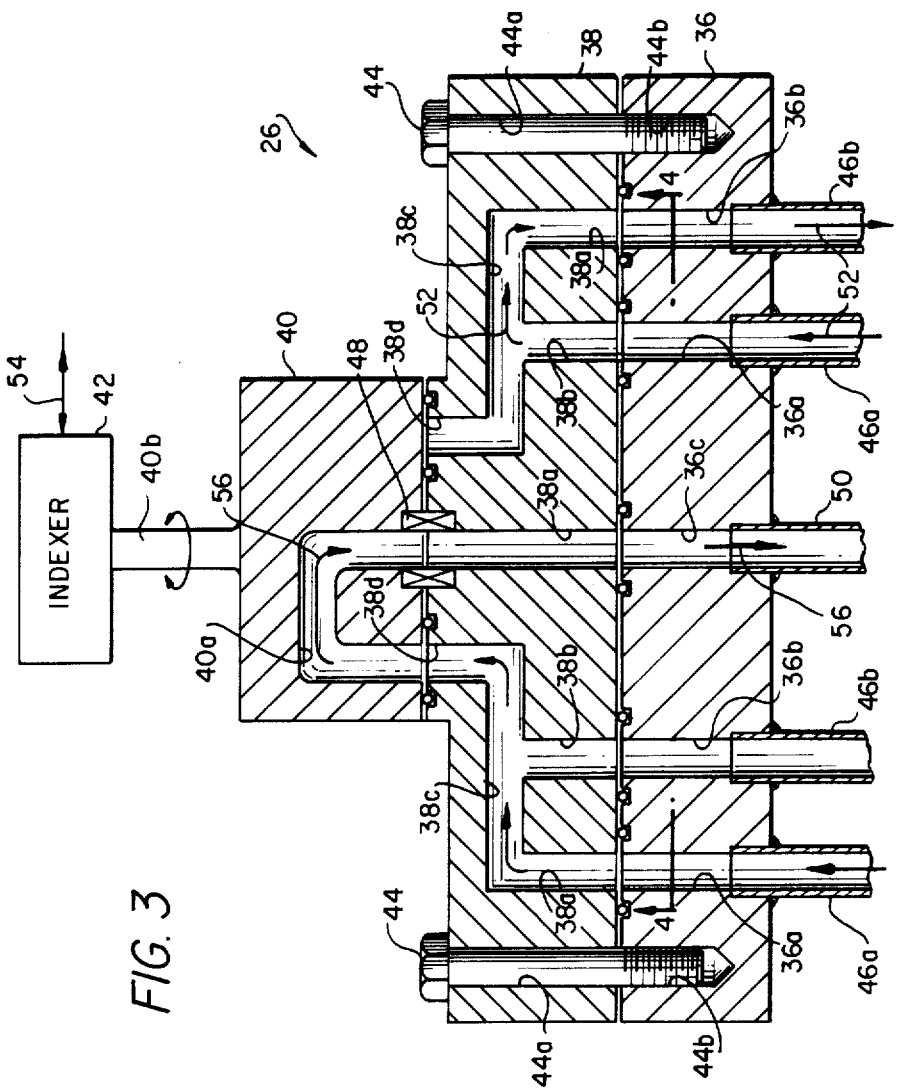
FIG. 3 is a sectional view of one of the multiport valves seen in FIG. 2.
Figure 4:
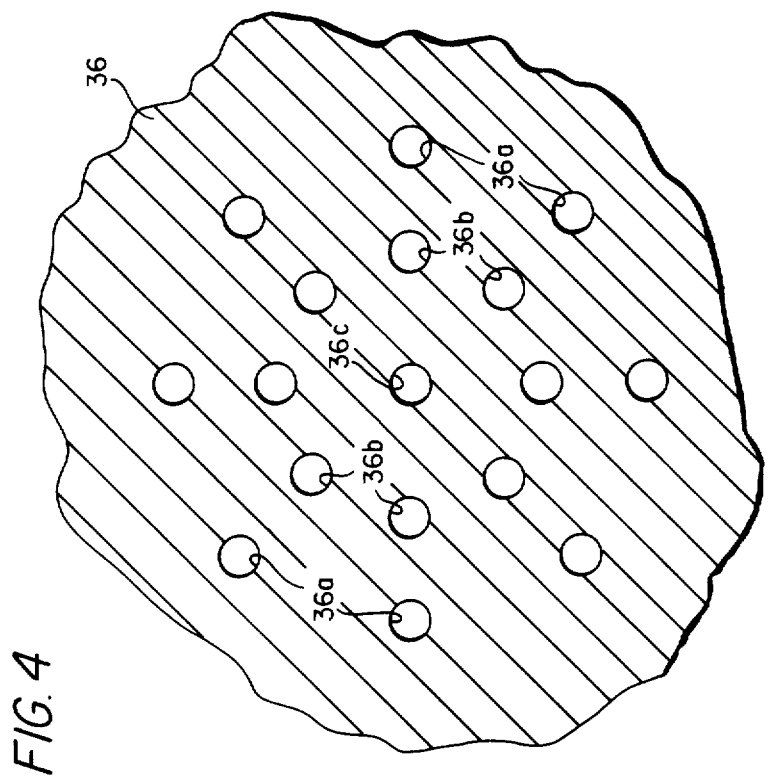
FIG. 4 is a sectional view taken along line 4—4 of FIG. 3.

As seen in FIG. 3, each multiport valve 26 is constructed having a manifold block 36, a valve block 38, a rotor 40, and an indexer or stepping motor 42. The valve block is secured to the manifold block by a circular array of bolts 44 extending through clearance bores 44a in the valve block and threaded into tapped bores 44b in the manifold block. The manifold block is formed with a plurality of angularly spaced pairs of radially aligned passages 36a and 36b (FIG. 4) which are countersunk at their illustrated lower ends to receive the ends of a pair of metal tubes 46a and 46b, respectively. Each manifold passage pair 36a and 36b, which respectively constitute valve inlet and outlet ports, communicates with a separate pair of valve block passages 38a and 38b, respectively, which are in communication at their upper ends with a cross passage 38c. Each of these latter passages is extended to present a circular array of angularly spaced outlet ends 38d in selective communication with the radially outer open end of a single inverted U-shaped passage 40a formed in rotor 40. The inner leg of this U-shaped passage is aligned with the rotor axis with its open lower end communicating with a centrally located valve block passage 38e via a union 48. This union also serves to mount rotor 40 to valve block 38 for bidirectional rotation by indexer 42 connected to the rotor via a rotor shaft 40b. The single, common central valve block passage 38a communicates with a single, common manifold block passage 36c (FIG. 4), whose lower end is countersunk to receive the end of a common outlet tube 50. Passage 36c constitutes the common outlet port of valve 26. Suitable seals, such as the illustrated O-ring seals, prevent fluid leakage at the interfaces of the manifold block, valve block, and rotor.

By joint reference to FIG. 1 and 3, it will be appreciated that each of the pairs of tubes 46a, 46b, manifold block passages 36a, 36b, and valve block passages 38a, 38b and 38c constitute one of the sample loops 32a–32g, 34a–34g. The continuous fluid flow through a sample loop of a stream which is not being sampled is illustrated by the arrows 52 in FIG. 3. By positioning rotor 40 to communicate its passage 40a with a selected one of the valve block passage outlets 38d as commanded by the associated sample selection subsystem computer 24 over data link 54, fluid flow in the selected sample loop is diverted to the path indicated by arrows 56. A sample is thus taken from the selected stream 10a–10g and directed by outlet tube 50 to spectrometer 28 for analysis. It is seen that the multiport valves accommodate continuous flow of fluid through the sample loops connected thereto, and thus a sample extracted from a selected sample loop is truely representative on a real-time basis of the fluid flowing in the associated process stream. In other words, none of the sample loops contains any dead fluid volume which would pertain to fluid flowing in a process stream at some time in the past. It will also be appreciated that the above described multiport valve construction facilitates servicing and replacement. That is, should a multiport valve fail, the operating parts thereof can be replaced without disturbing the sample loop connections by simply removing bolts 44 and replacing the valve body-rotor-indexer subassembly as a unit Downtime is thus minimized. Typically, valve outlet tubes 46b are connected back into the appropriate process stream, however in some cases they may simply be connected to waste.

Figure 2:
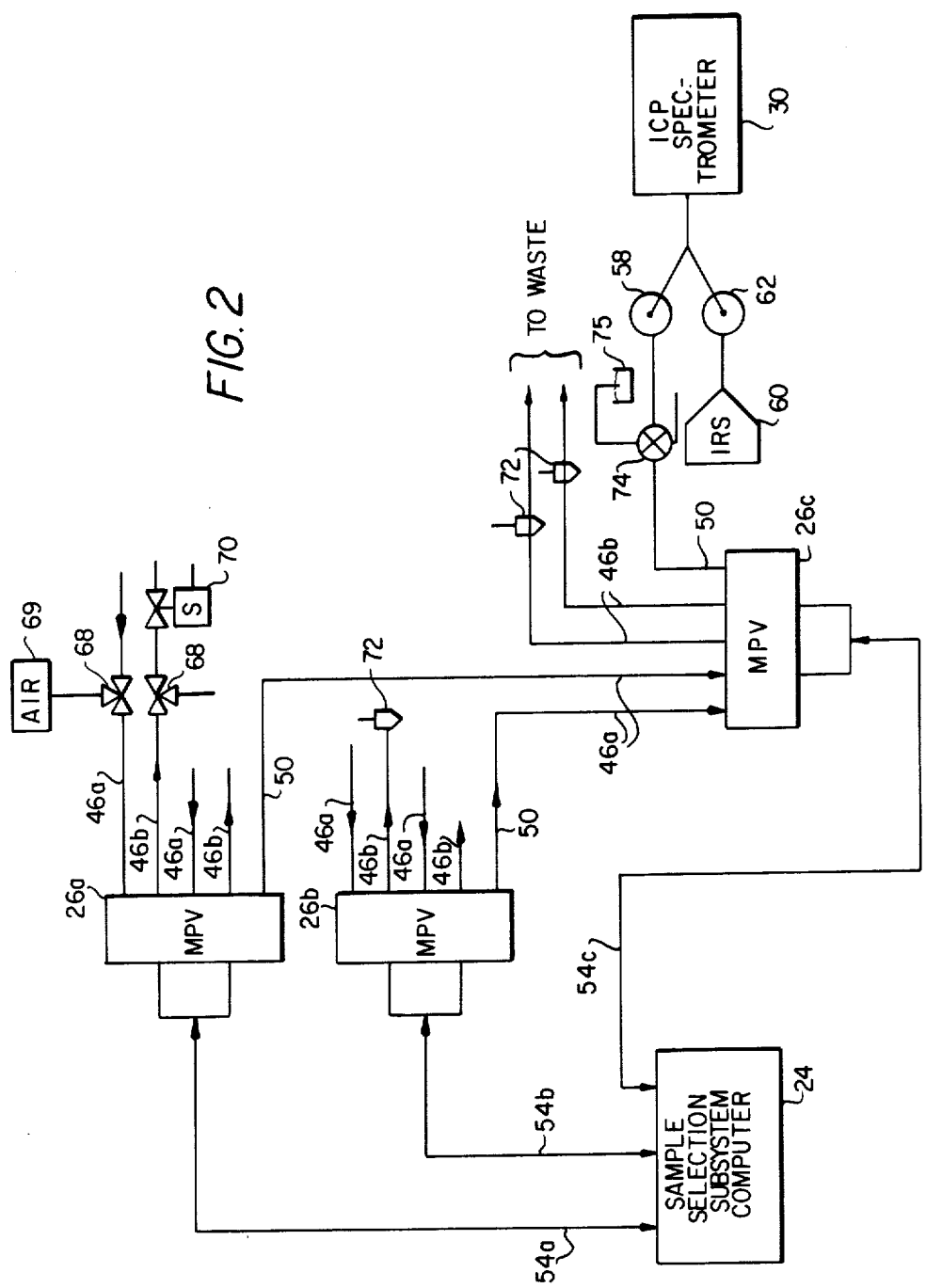
FIG. 2 is a schematic block diagram of a portion of one of the sample selection subsystems seen in FIG. 1.

As seen in FIG. 2, each sample selection subsystem 23A, 23B includes at least three multiport valves, indicated at 26a, 26b and 26c, which are all of the construction illustrated in FIG. 3. In some applications, such as those involving a large number of sample loops, more than three multiport valves would be implemented. Each multiport valve 26a, 26b, 26c responds to positioning commands selectively transmitted thereto over separate communication links 54a, 54b, 54c, respectively, by computer 24. Each multiport valve sends back valve position data over these links to verify that it has correctly responded to a computer command and to enable computer 24 to determine which direction the valve rotor should be rotated to reach the next selected valve position over the shortest path. It is seen from FIG. 2 that the various sample loops are shared between multiport valves 26a and 26b, with the common outlet ports (tubes 50) thereof connected to separate inlet ports (tubes 46a) of multiport valve 26c. It will be appreciated that valve 26c can readily accommodate sample inputs from more than the illustrated two multiport valves. The common outlet of multiport valve 26c is connected via tube 50 to a pump 58 which meters out a predetermined quantity of an extracted sample for injection into spectrometer 28. Mixed in with each injected sample is an internal reference standard solution metered out from a source 60 by a pump 62. The operations of pumps 58 and 62 are controlled by the instrument computer 30 seen in FIG. 2. The internal reference standard solution contains a predetermined concentration of a unique element which is not present in any of the process streams. By evaluating the response of spectrometer 28 to the presence of this unique element in each sample, computer 32 can minimize the effects of drift, analysis fluctuations and noise pursuant to developing analytical data of high reliability.

Referring jointly to FIG. 1 and 2, in addition to sample loops being connected with multiport valves 26a and 26b, one or more reservoirs 64 of a rinse solution are connected via tubes 64a to an inlet port 36a (FIG. 3) of each such valve of each sample selection subsystem 23A, 23B. Depending on the nature of the various process streams, the rinse solutions may consist of pure water and possibly an appropriate acid which are held in separate reservoirs 64 separately piped to different multiport valve inlet ports. Typically, the sample selection subsystem computers 24 would be programmed to schedule a rinse cycle immediately preceding and immediately following the taking of a sample for analysis by positioning valves 26a, 26b, 26c accordingly. Alternatively or additionally, these valves may be computer controlled to inject a water plug between extracted samples; these measures being taken to guard against cross-contamination of samples. Also connected to separate multiport inlets of both sample selection subsystems by individual tubes commonly indicated at 66a in FIG. 1 are plurality of containers commonly indicated at 66. Each of these containers holds a different solution containing a known concentration of each element the various samples are to be analyzed for. Thus, during a calibration or standardization routine, the multiport valves 26a, 26b, 26c of a selected sample selection subsystem are controlled by computer 24 to draw slugs of the various standards from containers 66 which are routed successively to spectrometer 28 and the responses thereto are evaluated. Computers 24 and 28 work in concert via interconnecting data link 31 to establish separate calibration curves for each spectrometer response to the known element concentration in each standards solution feed to the computer 30 over signal link 29. In addition, computer 30 automatically makes appropriate adjustments to the spectrometer to insure that the responses to each standards element is being properly recognized. In this manner, spectrometer 28 and computer 30 are effectively calibrated such as to provide analytical data specifically indicative of the concentrations of those elements or constituents of interest contained in each analyzed sample.

Returning to FIG. 2, at least some of the sample loops may include two-way valves 68 which are manually operated to interrupt fluid flow therethrough and connect a portion of the loop to a source 69 of air under pressure. In this way, blockages can be blownout with minimal interruption in service. Ideally, this blowout capacity is applied to all of the inlet and outlet ports of each multiport valve. In some instances, solenoid valves 70 are connected in line with tubes 46b communicating with the valve outlet ports. Specifically, these valves are incorporated in those of the valve outlet ports whose associated inlet ports are in communication with the various standards containers 66 via tubes 66a and the rinse reservoirs 64 via tubes 64a. These solenoid valves 70 are opened in response to signals from computers 24 during the periods rinse solutions and standard solutions are being routed through valves 26a, 26b and their common outlet ports to multiport valve 26c via tubes 50, thus to avoid pointless waste of these solutions. Also included in the valve outlet tubes 46b are flow switches 72 which serve to signal computers 24 that fluid flow in the sample loops is adequate for the taking of a sample and that an extracted sample has reached valve 26c and thus is available for analysis. These flow switches are among the process sensors generally indicated at 73 in FIG. 1 which further include sensors monitoring ongoing conditions within process 10, fluid levels within the standard containers 66 and rinse reservoirs 64, etc. Preferably, sample injection into the spectrometer is delayed for a sufficient equilibrium time after a flow switch signals adequate flow for the drawn sample to insure a representative sample and to further minimize any sampling cross-contamination. These flow switches further serve to indicate to computers 24 the existence of any blockages or restrictions to fluid flow.

As also indicated in FIG. 2, an electrically actuated three-way valve 74 remotely controlled by computer 24 is connected into the outlet tube 50 going from the common outlet port of multiport valve 26c to metering pump 58 to draw a sample from a specimen collected manually from a point in the process other than the monitored process streams 10a–10g. Thus, by entering the appropriate command at computer terminal 24a, valve 74 is positioned to draw a sample from a liquid specimen collected in a beaker 75. Analysis of this sample is performed in the same manner as the automatically drawn samples.

The analysis system 20 of FIG. 1 has a number of operating modes which are initiated by the operator at host computer 22 via its terminal 22a. In an operator selected setup mode, operating parameters for the sample selection subsystem computers 24 and the ICPS computers 30 are established. This includes setting up an analytical control table for each process stream 10a–10g to be sampled. These tables establish what the sample analysis for the various streams should be when the process is operating normally. Various levels of alarm limits are also established against which the various element concentrations indicated in each sample analysis are measured. Depending upon which limits the concentration of a particular element in a sample exceed, this fact is displayed at one of the sample selection subsystem computer terminals 24a and/or the host computer terminal 22a, printed out by the host computer printer 22b, and/or alarmed at the process computer terminal 12a. Sampling schedules are also entered into the sample selection subsystem computers 24 to set up the frequency at which the various process streams are to be sampled on a continuous basis, which may be on a time basis, e.g. once an hour, or on a sample count basis, e.g. once every twenty samples. Some process streams may be sampled on a demand basis rather than a continuous or automated basis. Sampling of a process stream which is included in the sampling schedule may be requested by an operator from any of the computer terminals 12a, 22a, and 24a, and a sample will be taken from the selected stream and analyzed out of order. The various process streams are prioritized and arranged in a sampling queue accordingly. Requests entered by an operator or generated automatically by the process computer 12 to sample a selected stream are given the highest priority.

The analytical data pertaining to all of the sample analyses are stored in the host computer for subsequent use in generating various reports and trend information such as selected element concentrations in a specified process stream as indicated by successive sample analyses taken over a specified period of time. Data on past sample analyses for any selected process stream or streams as may be retrieved and displayed or printed out on operator command. Host computer 22 coordinates the operations of sample selection subsystems 23A and 23B in order that the sampling load can be expeditiously shared between them. However, the subsystem computers 24 are programmed to go into a backup mode should the host computer go down, such that sampling and reporting to the process computer 12 can continue on a less flexible operating basis.

Either one of the sample selection subsystem computers may be put into a standardization mode during which standard samples are drawn from the various containers 66 and injected into spectrometer 28 pursuant to establishing calibration curves for all of the elements of interest. Each sample selection subsystem is capable of being put into a diagnostic mode during which an operator can manually troubleshoot the subsystem to determine if it is operating properly. As described above, either subsystem can be put into a single sample mode wherein an operator may request an analysis of any selected process stream. Also described above is the backup mode capability wherein the subsystems can carry on sample analysis during periods when host computer 22 is inoperative. Finally, in the fully automated mode, the subsystems perform sample analyses in totally operator-unattended fashion based on the formats established during the setup mode.

There are basically three classes of sample analyses, namely continuous or automated analyses, process control sample analysis requests, and operator sample analysis requests. During continuous analyses, samples are drawn according to the schedule established during the setup mode. Process control requests are those initiated automatically by the process computer 12 or manually via its terminal 12a to analyze a sample drawn from a specified process stream. Operator requests are those initiated at either of the computer terminals 22a and 24a to analyze a sample from a specified process stream or from a manually collected sample in beaker 75 (FIG. 2). An operator may also request that a specified standard sample be drawn to verify instrument calibration. These operator requests are of the highest priority and can be made at any time. Such requested samples are analyzed immediately upon completion of any analysis in progress.

Normally the two subsystems are both operating in their automated sampling mode as coordinated by host computer 22. However, at times one subsystem may be in a different mode, such as the diagnostics mode or the standardization mode. The other subsystem can continue in the automated sampling mode to generate the analytical data necessary to support process computer 12 in its process control capacity.

The automated multiple stream analysis system of the present invention may be applied to a wide variety of diverse process applications involving petroleum refining, petrochemical production, food and beverage processing, power generation, etc. By the same token, the analytical instrumentation may include visible, ultraviolet, infrared, X-ray and mass spectrometers; spectrophotometers; the various types of chromatographs; titrameters, densimeters; and so forth, as well as combinations thereof. An application for which the present invention is particularly suited is the fully automated process control of a nuclear fuel manufacturing facility including not only the fuel manufacturing process, but also the processes of recovering uranium from waste streams and waste stream treatment to reduce hazardous waste disposal costs. An analytical instrument highly suitable for this application is a Jarrell-Ash 9000 spectrometer, which is a multi-channel, direct-reading, optical emission spectrometer using an argon plasma to excite ionic and atomic particles. This instrument under the control of its ICPS computer can simultaneously analyze a sample for the concentrations of a multiplicity of elements of interest, such as uranium, boron, cadium, gadolinium, aluminum, calcium, chromium, iron, manganese, nickel, zinc and molybdenum, as well as an internal reference standard element such as scandium. Intel 80/24 microcomputers can be utilized as the sample selection subsystem computers, while the host computer may be a Digital Equipment Corporation 11/24 minicomputer. A typical sample analysis time may range from five to seven minutes which includes sample preparation, analysis and analytical data reporting.

It is thus seen that the objects set forth above, including those made apparent from the preceding description, are efficiently attained, and, since certain changes may be made in the above construction without departing from the scope of the invention, it is intended that all matter contained in the above description or shown in the accompanying drawings shall be interpreted as illustrative and not in a limiting sense.

Having described the invention, what is claimed as new and desired to secure by Letters Patent is:

1. An automated multiple stream analysis system comprising, in combination:
   A. a plurality of sample loops respectively connected in fluid communication with a plurality of process streams for accommodating continuous flow of sample fluids therethrough representive of the fluids flowing in the various process streams ona real-time basis;
   B. at least one multiport valve having a plurality of sets of interconnected inlet and outlet ports, each connected in series with a different one of said sample loops, a common outlet port, and means connecting any selected one of said inlet ports in fluid flow communication with said common outlet port for extracting a sample of the fluid flowing into said said selected inlet port and routing the flow of said extracted fluid sample to said common outlet port;
   C. an analytical instrument connected with said common outlet port to receive said extracted sample for immediate analysis;
   D. an instrument computer for developing analytical data pertaining to each sample analysis;
   E. a sample selection computer operating to automatically control said multiport valve connecting means to extract fluid samples from said sample loop in accordance with an operator established schedule and to compare said analytical data for each sample analysis with a corresponding analytical control table to signal if any of the element concentrations in an analyzed sample exceeds preestablished limits; and
   F. a process computer linked to said sample selection computer and operating in response to said analytical data to control the process involving the process streams.

2. The automated multiple stream analysis system analysis system defined in claim 1, which further includes at least one reservoir of a rinse solution connected with a separate inlet port of said multiport valve, said sample selection computer controlling said connecting means to draw a quantity of said rinse solution from said reservoir for delivery through said common outlet port to waste, thereby removing all vestiges of a previously extracted sample.

3. The automated multiple stream analysis system defined in claim 2, which further includes a plurality of containers, each holding a different standards solution containing a known concentration of each element to be found in the process streams and individually connected with a different inlet port of said multiport valve, said sample selection computer automatically controlling said connecting means to successively draw a standards sample from each said container for injection into said analytical instrument via said common outlet port for analysis, said instrument computer and said sample selection computer operating in concert to establish a separate calibration curve for each element to be analyzed for in said extracted samples.

4. The automated multiple stream analysis system defined in claim 3, which further includes means for drawing a sample from a manually collected specimen under the control of said sample selection computer in response to an operator request.

5. The automated multiple stream analysis system defined in claim 3, wherein said sample selection computer is programmed to accept operator requests to extract a sample from a sample loop of any selected process stream and to control said connecting means in extracting a requested sample at the earliest opportunity and in preference to the extraction of an automatically scheduled sample.

6. The automated multiple stream analysis system, defined in claim 5, wherein said connecting means is in the form of a rotor, and said multiport valve further includes a manifold block and a valve block removably secured to said manifold block and rotatably mounting said rotor, said manifold block including said sets of inlet and outlet ports and said common outlet port; said valve block including separate passages connecting said inlet and outlet ports of each said set in fluid communication, a separate extension of each said passage having an outlet end, and a single common passage communicating with said common outlet port; and said rotor including a single passage having an inlet end communicable with any one of said passage extension outlet ends and an outlet end communicating with said common passage; and indexing means for selectively angularly positioning said rotor to extract a sample from one of said passage extension outlet ends and convey said extracted sample to said common outlet port.

7. The automated multiple stream analysis system defined in claim 5, wherein said sample loops and said standards containers are connected with inlet ports of either one of first and second multiport valves, said rinse reservoir being connected with an inlet port of each said first and second multiport valves, and a third multiport valve having separate inlet ports individually connected with said common outlet ports of said first and second multiport valves and a common outlet port connected with said analytical instrument, said first, second and third multiport valves being automatically controlled by said sample selection computer.

8. The automated multiple stream analysis system defined in claim 5, wherein said multiport valve, said analytical instrument, said instrument computer and said sample selection computer compose a first subsystem, said analysis system further comprising a second subsystem of identical composition and a host computer coordinating the operations of said first and second subsystems whereby to share the sampling load therebetween.

9. The automated multiple stream analysis system defined in claim 8, wherein said sample loops connected with the process streams are connected in series with said multiport valves of both said first and second subsystems.

10. The automated multiple stream analysis system defined in claim 9, wherein said host computer is capable of controlling said first subsystems to extract said fluid samples in accordance with said established schedule while said second subsystem is being controlled to extract and analyze said standards samples pursuant to establishing said calibration curves.

* * * * *

UNITED STATES PATENT AND TRADEMARK OFFICE
CERTIFICATE OF CORRECTION

PATENT NO. : 4,722,830

DATED : February 2, 1988

INVENTOR(S) : Urie et al

It is certified that error appears in the above-identified patent and that said Letters Patent is hereby corrected as shown below:

On the title page Item [75] should read

--Inventors: Michael W. Urie, Wilmington, NC
William A. Young, Wilmington, NC
Frederick C. Schoenig, Wilmington, NC
Joel L. Pickett, Scotts Hill, NC
David R. McLemore, Springdale, Ohio --.

Signed and Sealed this

Twenty-first Day of June, 1988

Attest:

DONALD J. QUIGG

*Attesting Officer*

*Commissioner of Patents and Trademarks*